US012751669B2

(12) United States Patent
Hara

(10) Patent No.: US 12,751,669 B2
(45) Date of Patent: Oct. 6, 2026

(54) ELECTRODE CATHETER

(71) Applicant: INTER NOVA INC., Tokyo (JP)

(72) Inventor: Hiroshi Hara, Tokyo (JP)

(73) Assignee: Inter Nova Inc., Tokyo (JP)

(*) Notice: Subject to any disclaimer, the term of this patent is extended or adjusted under 35 U.S.C. 154(b) by 538 days.

(21) Appl. No.: 18/271,566

(22) PCT Filed: Jan. 18, 2022

(86) PCT No.: PCT/JP2022/001576
§ 371 (c)(1),
(2) Date: Jan. 17, 2024

(87) PCT Pub. No.: WO2022/172700
PCT Pub. Date: Aug. 18, 2022

(65) Prior Publication Data
US 2024/0138766 A1 May 2, 2024

(30) Foreign Application Priority Data
Feb. 9, 2021 (JP) ................................ 2021-018722

(51) Int. Cl.
*A61B 5/00* (2006.01)
*A61B 5/283* (2021.01)
(Continued)

(52) U.S. Cl.
CPC ............ *A61B 5/6852* (2013.01); *A61B 5/283* (2021.01); *A61B 5/367* (2021.01);
(Continued)

(58) Field of Classification Search
CPC ....... A61B 5/6852; A61B 5/283; A61B 5/367; A61B 18/14; A61B 18/1402;
(Continued)

(56) References Cited

U.S. PATENT DOCUMENTS 5,738,632 A * 4/1998 Karasawa ............ G01R 33/285 324/318
6,364,828 B1 * 4/2002 Yeung .................. A61B 1/0056 174/68.3

(Continued)

OTHER PUBLICATIONS

International Search Report issued Apr. 5, 2022 in connection with PCT/JP2022/001576.

*Primary Examiner* — Adam Z Minchella
(74) *Attorney, Agent, or Firm* — Blank Rome LLP

(57) ABSTRACT

Provided is an electrode catheter whose movable shape has a high reproducibility even when the load changes, and has a high degree of freedom in corresponding to the shape of a measurement site. The electrode catheter includes:
a catheter main body;
an operation handle connected to a base end side of the catheter main body; and
a tip end portion connected to a tip end side of the catheter main body,
wherein the tip end portion has:
an outer tube with a plurality of electrodes being provided and spaced apart on an outer circumferential surface thereof;
a coupling shaft with a plurality of pieces being coupled so that the pieces are able to mutually rotate within a predetermined range in a hollow space of the outer tube;
a head member connected to a tip end of the coupling shaft; and
a plurality of operation wires with one ends thereof being fixed to the head member and the other ends thereof being fixed to the operation handle,
wherein the pieces each have
a rotation shaft protruding in a direction orthogonal to an axis center of the coupling shaft;
(Continued)

a shaft receiving hole axially supporting the rotation shaft; and
a through hole that is located at a position offset from the axis center, and
wherein one of the operation wires is inserted through the through hole, and the tip end portion is allowed to be curved.

2 Claims, 6 Drawing Sheets

(51) Int. Cl.

| | |
|---|---|
| ***A61B 5/367*** | (2021.01) |
| *A61M 25/01* | (2006.01) |
| *A61N 1/05* | (2006.01) |
| *A61N 1/362* | (2006.01) |

(52) U.S. Cl.
CPC ..... *A61M 25/0136* (2013.01); *A61M 25/0147* (2013.01); *A61N 1/056* (2013.01); *A61N 1/362* (2013.01)

(58) Field of Classification Search
CPC ........ A61B 2018/1405–1437; A61M 25/0136; A61M 25/0147; A61N 1/056; A61N 1/362
See application file for complete search history.

(56) References Cited

U.S. PATENT DOCUMENTS

| | | | | |
|---|---|---|---|---|
| 10,751,177 | B2 * | 8/2020 | Morrissey | A61F 2/2436 |
| 2003/0125663 | A1 * | 7/2003 | Coleman | A61M 25/0136 604/95.04 |
| 2006/0184106 | A1 | 8/2006 | McDaniel et al. | |
| 2009/0099554 | A1 * | 4/2009 | Forster | A61F 2/2427 606/1 |
| 2019/0328212 | A1 | 10/2019 | Nakaji et al. | |

* cited by examiner

ELECTRODE CATHETER

CROSS-REFERENCE TO RELATED APPLICATIONS

This application is a national phase of PCT/JP2022/001576, filed Jan. 18, 2022, and claims priority to Japanese Patent Application No. 2021-018722, filed on Feb. 9, 2021, the entire contents of both of which are hereby incorporated by reference.

TECHNICAL FIELD

The present invention relates to a minimally invasive electrode catheter capable of being curved near the tip end thereof.

BACKGROUND ART

Conventionally, various electrode catheters have been used as medical devices for diagnosing or treating cardiac arrhythmias. For example, as shown in FIGS. 9 to 12, there is an electrode catheter 100 capable of being curved by deflecting a tip end portion 102 of the catheter. FIG. 10 is a partial longitudinal cross-sectional view of a catheter main body 101, FIG. 11 is a horizontal cross-sectional view of the catheter main body 101 taken by a line X-X in FIG. 10, and FIG. 12 is a longitudinal cross-sectional view of a tip end portion 102. This electrode catheter has the flexible tubular catheter main body 101, the tip end portion 102 connected to the distal end of the catheter main body, an operation handle 103 connected to the proximal end of the catheter main body, and a plurality of puller wires 104 whose proximal ends are fixed to the operation handle, and distal ends are fixed to the tip end portion (see Patent document 1).

While the catheter main body 101 is flexible and can be bended, it cannot be compressed in the longitudinal axial direction. In this way, by rotating the operation handle 103, the tip end portion will rotate accordingly.

The tip end portion 102 has a synthetic resin-made tube portion 105 that is more flexible than the catheter body, and has thereinside a deflection structural body 106 for biasing the tip end portion 102 so as to deflect the same. The deflection structural body is a flat strip-shaped member, and this flat strip-shaped member is made of a flexible metal. Such strip-shaped metal when used serves as an axis of the shape, and prevents shape change i.e. so-called heat sagging observed over time after the catheter has been indwelled in the heart.

The tube portion 105 at the tip end portion has a plurality of off-axis lumens 107 which are positioned diametrically opposite to each other across the deflection structural body. Inserted through each of these opposing lumens is the puller wire 104 for changing the orientation of the tip end portion. Further, the tube portion has another lumen 108 for inserting an electrode lead wire 111 of the tip end portion. The outer diameter of the tube portion is not larger than 8 Fr (about 2.7 mm), as is the case with the outer diameter of the catheter main body. A tip end electrode 109 is attached to the distal end of the tip end portion. Also, there are attached a plurality of ring electrodes 110 along the longitudinal axial direction of the tip end portion. Individual electrode lead wires 111 are connected to the tip end electrode and the ring electrodes. Each lead wire is passed through the lumen 108 of the tip end portion, a central lumen 112 of the catheter main body, and the inner region of the operation handle, and is connected to a connector 113 provided at the operation handle end. A suitable monitor, a power supply or other necessary equipments can be connected to this connector. Since there is no member provided thereinside that serves as an axis, shape change i.e. so-called heat sagging is likely to occur over time after the catheter has been indwelled in the heart.

Two puller wires 104 extend from the operation handle, and are passed through the central lumen 112 of the catheter main body before being inserted through the off-axis lumens 107 of the tip end portion. The proximal end of each puller wire is fixed to the operation handle, and the distal end of each puller wire is fixed to the tip end electrode 109. Further, there are provided inside the catheter main body two compression coils 114 surrounding each puller wire. This structure allows the tip end portion to be deflected in both directions by operating the operation handle. That is, when either puller wire is moved in the longitudinal axial direction with respect to the catheter main body, the tip end portion can be deflected in the direction of a side surface of the tip end portion to which the puller wire is fixed, thereby allowing the tip end portion to be curved (see paragraph 0040 of Patent document 1).

In endoscopes, which are not electrode catheters but are similar medical devices, the following curving component is used. There is known a curving component for use in endoscope that has a plurality of curving pieces which are mutually rotatable and whose abutting portions provided at the end portions thereof facing the longitudinal axial direction are capable of abutting against each other, in which the plurality of curving pieces are provided in a consecutive manner along the longitudinal axial direction. Specifically, each curving piece includes an annular wall portion having an inner and an outer circumferential surface around the longitudinal axis, and having a given length along the longitudinal axial direction; a plurality of wire insertion portions whose wall portions each have a first wall thickness, and whose through holes formed thereon penetrate the abovementioned wall portions in the longitudinal axial direction and allow traction wires for rotating the curving pieces to be inserted therethrough; thin-walled portions that are provided at wall portions between the plurality of wire insertion portions around the longitudinal axis, and each have a second wall thickness which is formed thinner than the first wall thickness; and a thick-walled portion which is a wall portion at a site different from the thin-walled portions between the plurality of wire insertion portions around the longitudinal axis, and has a third wall thickness that is even thicker than the second wall thickness (see paragraph 0021, FIG. 2 of Patent document 2).

PRIOR ART DOCUMENTS

Patent Documents

Patent document 1: JP-A-2006-255401
Patent document 2: WO2018/146852

SUMMARY OF THE INVENTION

Problems to be Solved by the Invention

According to the electrode catheter of the abovementioned Patent document 1, while the tip end portion of the catheter is allowed to be curved, since the curving curvature depends on the designed curvature of the deflection structural body, the deflection structural body needs to be designed to fit the shape of a measurement site. Further, in order to control the deflection of the deflection structural body at the tip end portion, there are provided inside the catheter main body two compression coils surrounding the first and second puller wires; however, whenever a load is applied to the tube portion which is an outer tube, a distortion may occur in the movable shape, which has resulted in a problematic reproducibility of curving curvature. Furthermore, each compression coil needs to be attached manually one by one, which has led to a problem of low workability. In addition, since the mechanism of the current catheters in general is such that the tube is to be forcibly bended by pulling a puller wire, shortening a bending distance of the tube will result in a high tensile load when bending the front end, which has technically caused the radius at the time of bending to be limited to 2 cm.

Further, as for the abovementioned curving component of the Patent document 2, while the curvature of the curving component composed of the curving pieces can be changed as a whole, the curving component does not involve a concept of changing the curvature in accordance with the shape of a measurement site as is the case with an electrode catheter as this curving component is intended for endoscopic use. Therefore, there is no freedom at all in terms of achieving a different and appropriate curvature per each site, and there has been a problem in applying the configuration of such curving component to an electrode catheter. Moreover, the curving piece of an endoscope has a hollow structure for inserting a forceps thereinto due to its intended use, which is different from a structure allowing electrodes to be placed on the outer circumferential surface thereof.

In view of the problems with these conventional technologies, the present invention is to provide an electrode catheter that can reproducibly realize a curved shape corresponding to the shape of a measurement site, and can realize a required curved shape with a high degree of freedom. It is also an object of the present invention to realize an electrode catheter that can be manufactured easily and at a low cost.

Means to Solve the Problems

The present invention is an electrode catheter including:
- a catheter main body;
- an operation handle connected to a base end side of the catheter main body; and
- a tip end portion connected to a tip end side of the catheter main body,
- wherein the tip end portion has:
- an outer tube with a plurality of electrodes being provided and spaced apart on an outer circumferential surface thereof;
- a coupling shaft with a plurality of pieces being coupled so that the pieces are able to mutually rotate within a predetermined range in a hollow space of the outer tube;
- a head member connected to a tip end of the coupling shaft; and
- a plurality of operation wires with one ends thereof being fixed to the head member and the other ends thereof being fixed to the operation handle, wherein the pieces each have
- a rotation shaft protruding in a direction orthogonal to an axis center of the coupling shaft;
- a shaft receiving hole axially supporting the rotation shaft; and
- a through hole that is located at a position offset from the axis center, and wherein one of the operation wires is inserted through the through hole, and the tip end portion is allowed to be curved by operating the operation wires via the operation handle. Further, the electrode catheter of the present invention may also be such that a plurality of pieces having different dimensions in an axial direction are coupled to correspond to the shape of a measurement site. Furthermore, the electrode catheter of the present invention may also be such that a cutout is provided on an outer circumferential surface of each piece to form a gap between the cutout and an inner circumferential surface of the outer tube, and a lead wire of the electrode is placed in the gap.

Effects of the Invention

According to the electrode catheter of the present invention, there can be reproducibly realized a curved shape corresponding to the shape of a measurement site, and there can be realized a required curved shape with a high degree of freedom. Further, there can be realized an electrode catheter that can be manufactured easily and at a restricted cost.

MODE FOR CARRYING OUT THE INVENTION

The embodiment of the present invention is described hereunder with reference to each working example.

Example 1

Figure 1:
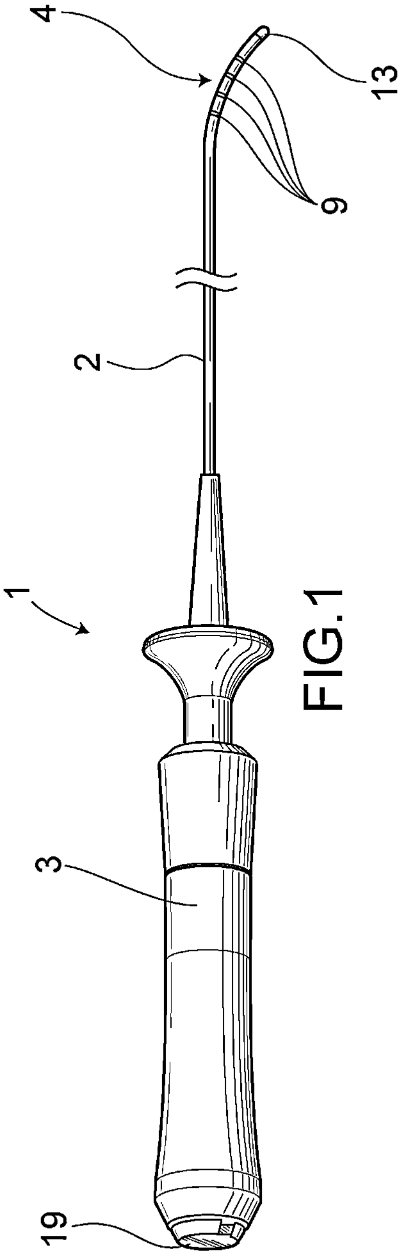
FIG. 1 is an external perspective view showing an electrode catheter of an example 1 of the present invention.
Figure 2:
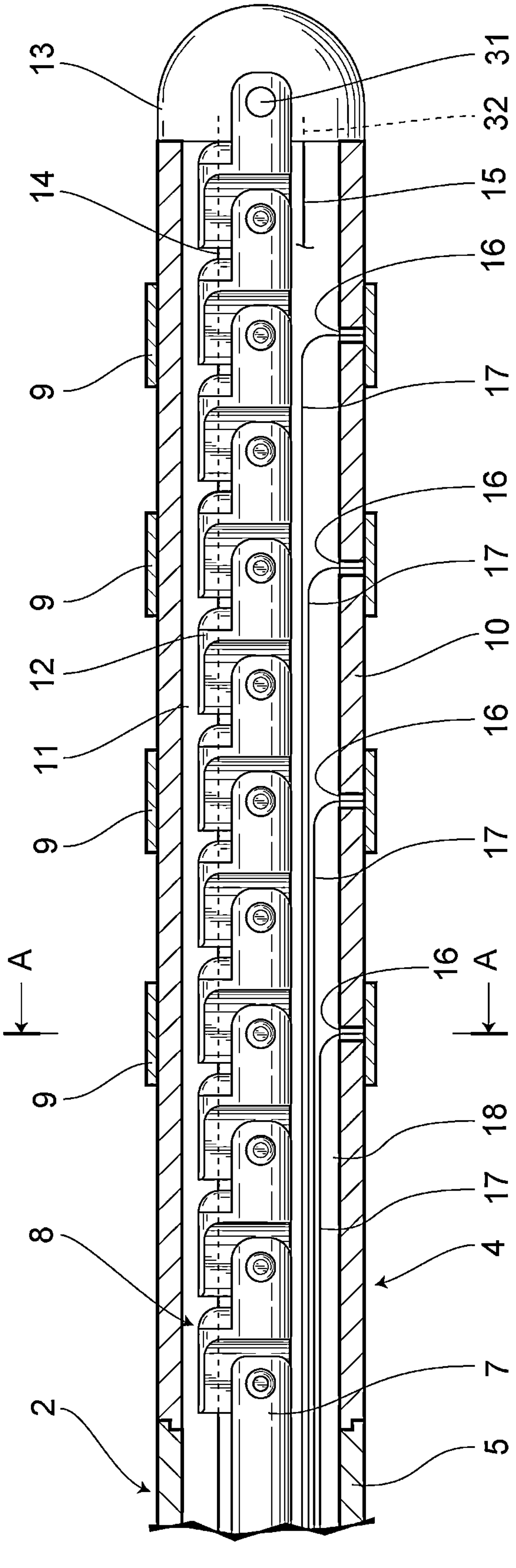
FIG. 2 is a longitudinal cross-sectional view showing a tip end portion of the electrode catheter of the example 1.
Figure 3:
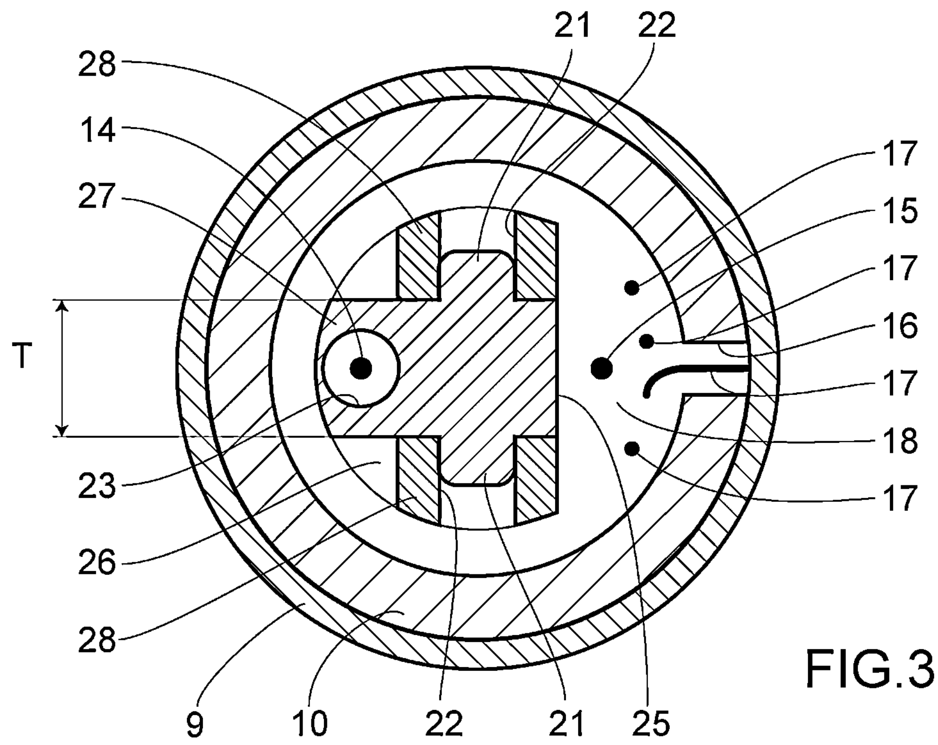
FIG. 3 is a horizontal cross-sectional view showing the tip end portion of the electrode catheter of the example 1.

FIG. 1 is an external perspective view showing an example 1 of an electrode catheter of the present invention. FIG. 2 is a longitudinal cross-sectional view of a tip end portion of the electrode catheter of the present invention, and FIG. 3 is a horizontal cross-sectional view of such tip end portion that is taken by a line A-A in FIG. 2. The schematic structure of an electrode catheter 1 of the present invention is substantially the same as that of the electrode catheter disclosed in Patent document 1, which is the conventional technology. That is, the electrode catheter of the present invention has a flexible tubular catheter main body 2, an operation handle 3 connected to the base end side of this catheter main body 2, and a flexible synthetic resin tip end portion 4 connected to the tip end side of the catheter main body 2. Since the operation handle 3 is not different from the operation handle in the conventional technology, the description thereof is omitted. Here, in the following descriptions, specific dimensions are given to certain parts of members for the purpose of making it easier to understand the structure of each member; however, the specific dimensions mentioned shall not limit or affect the interpretation of the technical scope of the invention in any way.

An outer tube member 5 composing the catheter main body 2 is not different from the tube member in the conventional technology. The operation handle 3 is connected to the base end side of the tube member 5, and the tip end portion 4 is connected to the tip end side of the tube member 5. The tube member 5 is made of a flexible synthetic resin material such as polyolefin, polyamide, polyether polyamide, or polyurethane. The internal structure of the catheter main body 2 differs significantly from that of the electrode catheter of the conventional technology. That is, the internal structure of the catheter main body 2 does not include two compression coils surrounding a plurality of puller wires as in the conventional technology. Further, a support shaft 7 having a plurality of lumens is placed inside the tube member 5. The base end side of the support shaft 7 is fixed to the operation handle 3, and a coupling shaft 8 composing the tip end portion of the catheter is connected to the tip end side of the support shaft 7.

Described hereunder is the tip end portion 4 which is the characteristic configuration of the electrode catheter of the present invention. The tip end portion 4 has an outer tube 10 with a plurality of ring electrodes 9 being provided and spaced apart on the outer circumferential surface thereof; the coupling shaft 8 with a plurality of pieces 12 being coupled so that they are able to mutually rotate within a predetermined range in a hollow space 11 of the outer tube 10; a head member 13 connected to the tip end of the coupling shaft 8; and a plurality of operation wires 14, 15 with one end(s) thereof being fixed to the head member 13 and the other end(s) thereof being fixed to the operation handle 3.

The outer tube 10 is made of a biocompatible synthetic resin material such as polyurethane, polyethylene or the like. The outer diameter of the outer tube 10 is not larger than 8 Fr (about 2.7 mm) as is the case with the outer diameter of the catheter main body 2, preferably not larger than 6 Fr (about 2.00 mm). The outer tube 10 is made as a more flexible tube than the catheter main body 2. As shown in FIG. 2, on the outer circumferential surface of the outer tube 10, there are attached the plurality of ring electrodes 9 that are arranged at predetermined intervals in the longitudinal direction. Although only four ring electrodes 9 are shown in FIG. 2, the number of the ring electrodes 9 attached is arbitrary. For example, the number may be 6 to 20, preferably 8 to 12. Each ring electrode 9 is fixed to the outer tube 10 using a curable adhesive. The ring electrodes are made of a metallic material with a favorable electrical conductivity, such as gold, platinum, iridium or the like, and is preferably made of platinum or its alloys, which have an excellent X-ray imaging property when the electrode catheter is used. Formed on the tube wall of the outer tube 10 are side holes 16 corresponding to the positions where the ring electrodes 9 are to be fixed. A lead wire 17 is connected to the inner circumferential surface of each ring electrode 9 at the location corresponding to the side hole 16. An insulation coated metal electrical wire is used as the lead wire 17, where only the coating at the end portion thereof that is to be connected to the ring electrode 9 is stripped off so as to allow the metal core wire to be welded to the inner circumferential surface of the ring electrode 9. The lead wire 17 inserted through the side hole 16 is introduced into a gap 18 formed between the coupling shaft 8 and the inner wall of the outer tube 10, and is connected to a connector 19 provided at the operation handle 3 through the inner space of the catheter main body 2. The outer diameter of the coated lead wire 17 is about 0.06 to 0.1 mm, which is not thick; however, in terms of installing a plurality of lead wires 17, a larger space formed between the outer surface of the coupling shaft 8 and the inner circumferential surface of the outer tube 10 leads to a better workability. For this reason, a cutout 25 is provided on the outer circumferential surface of the piece 12 as a composing element(s) of the coupling shaft 8, and the gap 18 substantially having a half-moon shape when viewed in a cross-section is formed between the cutout 25 and the inner circumferential surface of the outer tube 10. An operation wire 15 is also inserted through this gap 18, and the end portion of this operation wire 15 is fixed to the operation handle 3.

Figure 4:
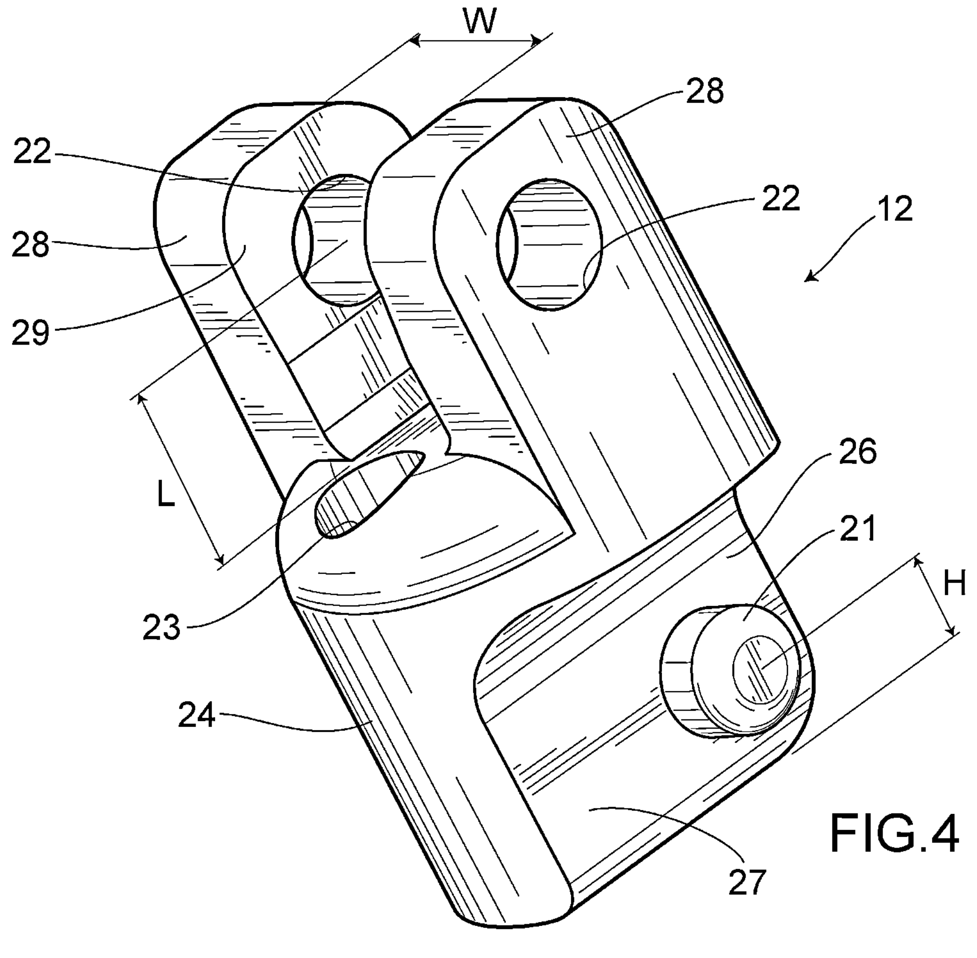
FIG. 4 is a perspective view showing a piece of the electrode catheter of the example 1.

The coupling shaft 8 is made up of the plurality of identically shaped pieces 12 that are coupled together so that they are able to mutually rotate within a predetermined range. As shown in FIG. 4, the pieces 12 as the composing elements of the coupling shaft 8 each have a rotation shaft 21 protruding in a direction orthogonal to an axis center of the longitudinal direction; a shaft receiving hole 22 axially supporting the rotation shaft 21 of an adjacent piece; and a through hole 23 that is formed in the axial direction and is located at a position offset from the axis center.

A lower half portion 24 of the piece 12 in the longitudinal direction has the cutout 25 formed on one side surface of a cylindrical shape with an outer diameter of 1.7 mm. Further, the short shaft 21 protruding in the direction orthogonal to the axis center of the longitudinal direction is provided on both side surfaces perpendicular to the cutout 25, and a space 26 having the shape of a cutout is provided around the short shaft 21. That is, in the lower half portion 24 of the piece 12 in the longitudinal direction, there is formed a central plate portion 27 perpendicular to the cutout 25, and the short shaft 21 is provided on and protrudes from both surfaces of such central plate portion 27. A dimension H from the center of the short shaft 21 to a lower end surface is formed as 0.4 mm, and a thickness T of the central plate portion 27 is formed as 0.7 mm. Further, the circumferential side surface of the shaft end of the short shaft 21 is rounded in the shape of R. Furthermore, the through hole 23 in the axial direction is provided at the position offset from the axis center.

In the upper half portion of the piece 12 in the longitudinal direction, there is formed a pair of support arm portions 28 corresponding to the positions where the short shafts 21 in the lower half portion are provided, and a clearance W between these paired support arm portions 28 is formed as 0.7 mm. This clearance W corresponds to the thickness T of the central plate portion 27, but is formed slightly larger than the thickness T of the central plate portion 27. Further, the paired support arm portions 28 are each provided with the shaft receiving hole 22 that is formed at a position orthogonal to the axis center of the longitudinal direction, and the inner diameter of the shaft receiving hole 22 is formed slightly larger than the outer diameter of the short shaft 21. Moreover, while the clearance W is formed as 0.7 mm at the central portions of the shaft receiving holes 22, it is formed as 0.71 mm at the upper end portions of the support arm portions 28. That is, a gently inclined surface 29 is formed on the inner surface of each of the paired support arm portions 28. In this way, the central plate portion 27 in the lower half portion can be easily fit between the paired support arm portions 28. In addition, a dimension L from the center of the shaft receiving hole 22 to the upper end surface of the lower half portion is formed as 0.55 mm.

Figure 5:
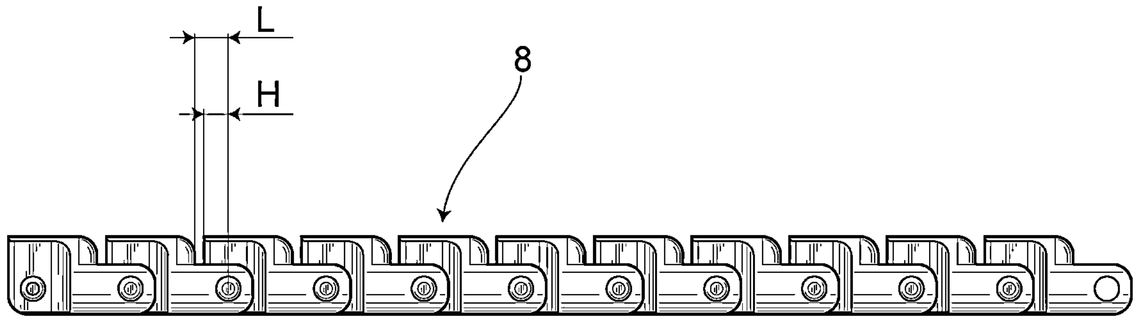
FIG. 5 is a side view showing a coupling shaft when it is in a linear state.
Figure 6:
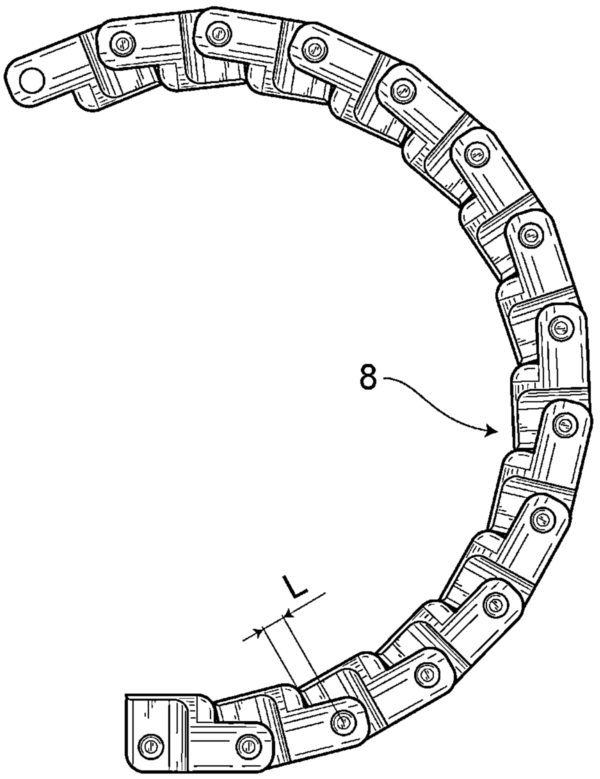
FIG. 6 is a side view showing the coupling shaft when it is in a curved state.

This means that in the coupling shaft 8 with the plurality of pieces 12 being coupled together, there exists a gap of 0.15 mm between the adjacent pieces 12, 12, which is the difference between the dimension L and the dimension H, thereby allowing the short shafts 21 of the adjacent pieces 12 that are supported by the shaft receiving holes 22 to rotate within a predetermined range. A rotatable range is determined by the size of the gap. FIG. 5 is a side view of the coupling shaft 8 when it is in a linear state, and FIG. 6 is a side view of the coupling shaft 8 curved leftward as a result of pulling the operation wire 14 on the left side of the coupling shaft 8 toward the base end side. If the gap as the difference between the dimension L and the dimension H is large, a larger rotation range will be achieved, and a curvature radius when the coupling shaft 8 has been curved the most can be reduced. In contrast, if the gap is small, a smaller rotation range will be achieved, and the curvature radius when the coupling shaft 8 has been curved the most will increase. In this way, by coupling the plurality of pieces 12 having different dimensions in the axial direction, there can be realized a movable shape with a high degree of freedom in corresponding to the shape of a measurement site.

The piece 12 is made as one piece by injection molding using a biocompatible synthetic resin material such as engineering plastics mainly including, for example, polyacetal, polyethylene, ABS, nylon and polyurethane; and super engineering plastics mainly including, for example, PEEK, PPS and PSU. This brings about an advantage of allowing a mass production effect to be easily achieved. The process of coupling together the pieces 12, 12 is performed by taking advantage of the elastic deformation property of an injection-molded product made of a synthetic resin material. In other words, of two pieces 12 that are to be coupled together, the central plate portion 27 of one of the pieces 12 is pushed and fitted into the clearance W between the inner surfaces of the support arm portions 28 of the other piece 12. There, since the gently inclined surface 29 is formed on the inner surface of the support arm portion 28 of each piece, and since the circumferential side surface of the shaft end of the short shaft 21 provided on both surfaces of the central plate portion 27 of each piece is rounded in the shape of R, by pushing in the piece in the longitudinal direction, the R-shaped part formed on the circumferential side surface of the shaft end of the short shaft 21 will cause the clearance W between the inner surfaces of the support arm portions 28 of the piece to be temporarily widened so that the short shafts 21 can be fitted into the shaft receiving holes 22.

The head member 13 has a shape established by slightly extending the lower portion of a substantially semispherical head portion thereof, and is connected to the upper end portion of the coupling shaft 8. As such, the head member 13 has a structure that allows it to be coupled to the uppermost piece composing the coupling shaft 8. That is, the side surfaces of the head member 13 are provided with a pair of short shafts 31 capable of being fitted into the shaft receiving holes 22 of the uppermost piece of the coupling shaft 8. Further, provided on the lower surface of the head member 13 are fixing holes 32 for inserting and fixing the operation wires 14, 15, where the terminal ends of these operation wires 14, 15 are fixed to the fixing holes 32 using an adhesive.

Figure 7:
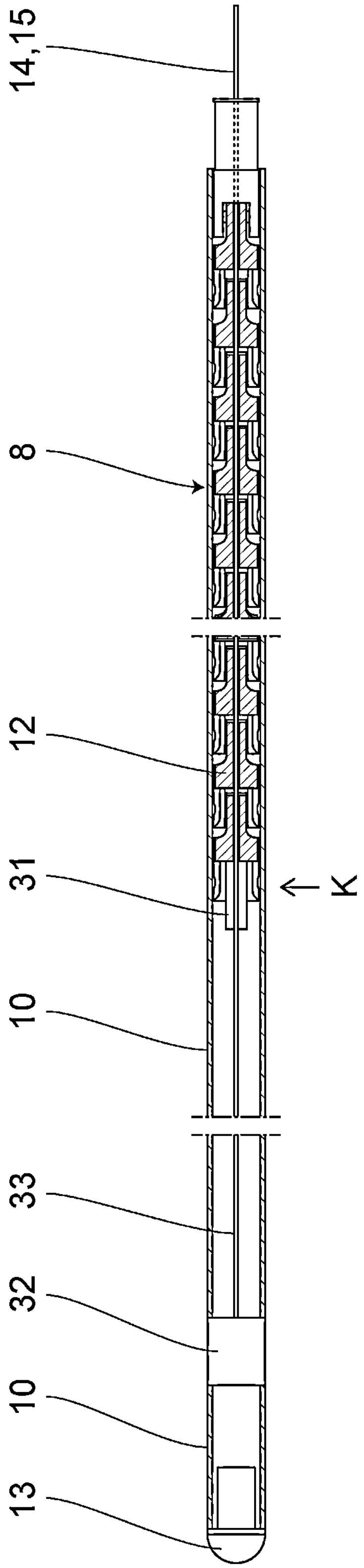
FIG. 7 is a cross-sectional view showing the tip end portion in which a bending point is arranged before a head member.

Furthermore, as shown in FIG. 7, in a region between the coupling shaft 8 composed of the plurality of pieces 12 and the head member 13, the outer tube 10 is provided with a wire terminal end member 31 whereby a bending point K can be arranged before the head member 13. This results in a flexibility of the outer tube 10 ranging from the head member 13 to the wire terminal end member 31, whereby the occurrence of cardiac tamponade is expected to be reduced. Moreover, since there is no need to install a structure for bending the tip end portion inside the region of the outer tube 10 that ranges from the head member 13 to the wire terminal end member 31, there is created a space to place a shape-memory alloy as typified by NT alloy, which allows for the placement of ring, basket, PentaRay or other tip end shapes used in pulmonary vein arrhythmia measurement. The outer tube 10 and the wire terminal end member 31 are bonded together by an adhesive, and the operation wires 14, 15 are fixed to the wire terminal end member 31. This configuration allows the bending point K to be provided at where the wire terminal end member 31 is provided, and the tip end portion to be bended by operating the operation wires 14, 15. Here, in FIG. 7, 32 indicates an electrode for pacing, and 33 indicates an electrical wire for pacing.

As the operation wires 14, 15, there may be used operation wires known in the conventional art. That is, there may be used an operation wire that is made of a wire material such as stainless steel, NT or the like, and has had its surface coated with a low-friction material such as Teflon (registered trademark). Further, there may also be used an engineering plastic material such as polyetheretherketone. As the wire diameter of the operation wire, preferred is a wire diameter of 0.1 to 0.4 mm.

According to the electrode catheter described above, the coupling shaft is allowed to be curved by operating the operation handle, and the flexible tip end portion 4 externally attached to the coupling shaft can be reproducibly curved as it is configured to correspond to the shape of a measurement site.

Example 2

An example 2 is suitable for realizing a catheter with a smaller diameter as compared to the electrode catheter of the example 1. With the example 1, while, for example, a catheter of up to 6 Fr (about 2.0 mm) can be realized without difficulty, it is not easy to realize a catheter of 5 Fr (about 1.67 mm) or smaller. In this regard, the example 2 is one in which even a small-diameter catheter can be easily realized by devising the shape of the piece(s) composing the coupling shaft.

Figure 8C:
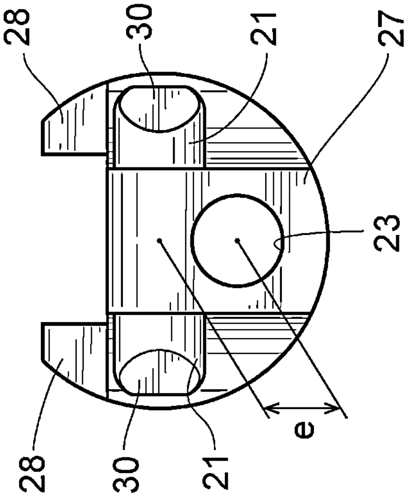
FIG. 8C is a view taken along a direction Z shown in FIG. 8A.
Figure 8B:
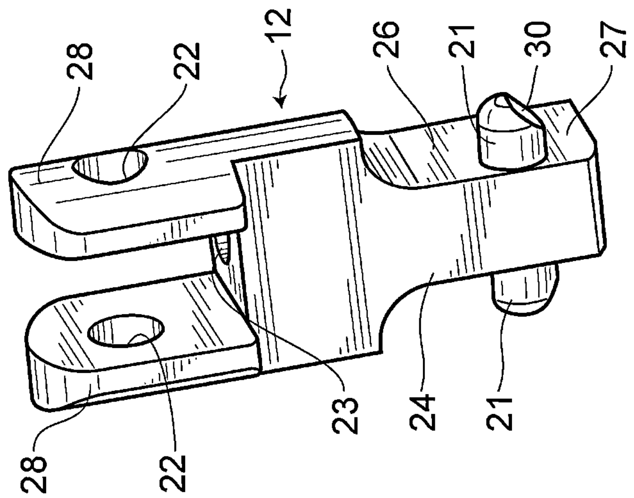
FIG. 8B is a perspective view showing a piece of the electrode catheter of the example 2.
Figure 8A:
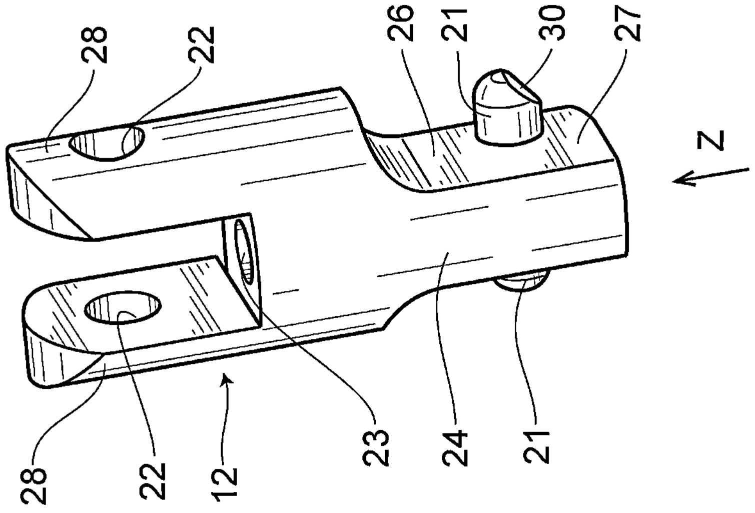
FIG. 8A is a perspective view showing a piece of an electrode catheter of an example 2.
Figure 9:
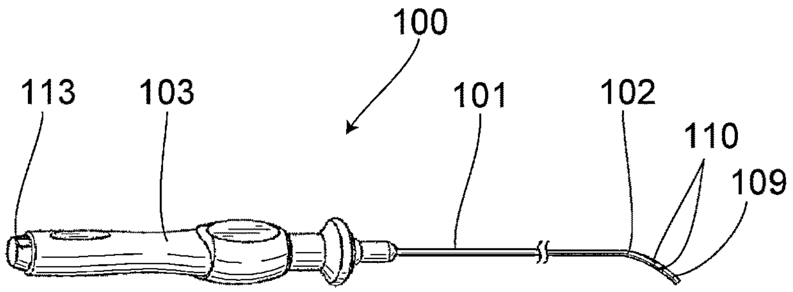
FIG. 9 is an external perspective view showing an electrode catheter of the conventional art.
Figure 10:
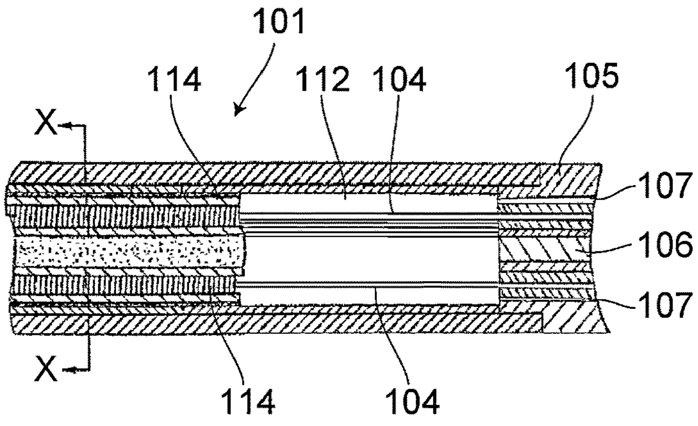
FIG. 10 is a partial longitudinal cross-sectional view showing a catheter main body of the conventional art.
Figure 11:
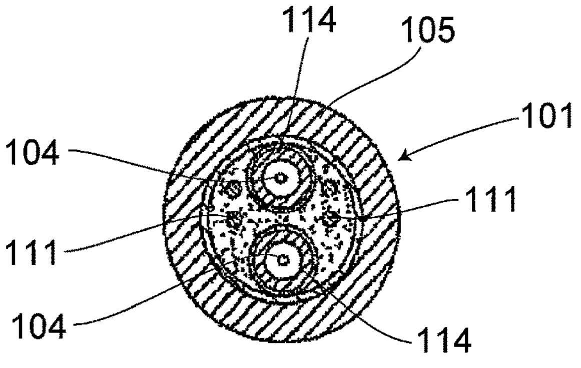
FIG. 11 is a horizontal cross-sectional view showing the catheter main body of the conventional art.
Figure 12:
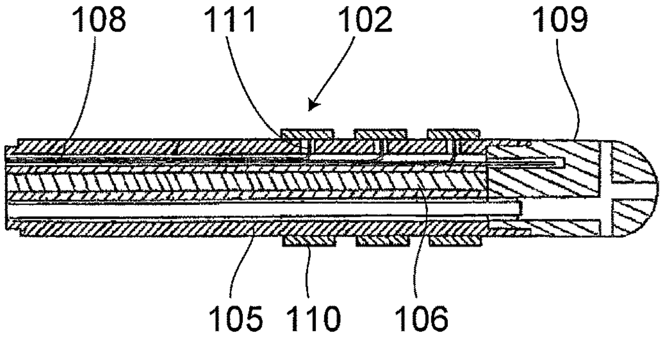
FIG. 12 is a longitudinal cross-sectional view showing a tip end portion of the electrode catheter of the conventional art.

FIGS. 8A, 8B and 8C show the appearance of the piece 12 used in an electrode catheter of the example 2, where FIG. 8A is a perspective view taken from a side where the cutout 25 is not provided, FIG. 8B is a perspective view taken from a side where the cutout 25 is provided, and FIG. 8C is a view taken along a direction Z shown in FIG. 8A. This piece 25 has the same basic configuration as the piece in the example 1. That is, the lower half portion 24 of the piece 12 in the longitudinal direction has the cutout 25 formed on one side surface, and the short shaft 21 protruding in the direction orthogonal to the axis center of the longitudinal direction is provided on both side surfaces perpendicular to the cutout 25. Further, the space 26 having the shape of a cutout is provided around the short shaft 21, and there is formed the central plate portion 27 perpendicular to the cutout 25. Moreover, the through hole 23 in the axial direction is provided at the position offset (e) from the axis center of the longitudinal direction. In addition, in the upper half portion of the piece 12, there is formed the pair of support arm portions 28 corresponding to the positions where the short shafts 21 in the lower half portion are provided, and the paired support arm portions 28 are each provided with the shaft receiving hole 22 that is formed at the position orthogonal to the axis center of the longitudinal direction. Although the piece in the example 2 and the piece in the example 1 share the above configuration, they differ from each other in the following aspects.

The outer diameter of the piece 12 in the example 2 is smaller than the outer diameter of the piece in the example 1. Specifically, while the outer diameter of the piece in the example 1 is 1.7 mm, the outer diameter of the piece in the example 2 is 1.3 mm. The offset (e) from the axis center of the through hole 23 in the example 2 is smaller than the offset in the example 1. Further, the cutout 25 of the piece 12 in the example 2 is provided only in the lower half portion 24, because a smaller outer diameter of the piece results in a thinner wall thickness of a certain part around the shaft receiving hole 22 provided at the support arm portion 28. Moreover, a chamfer 30 as an inclined surface is provided on the lower side of the end portion of each short shaft 21 formed on both surfaces of the central plate portion 27. In addition, the length of the central plate portion 27 of this piece in the axial direction is larger than that of the piece in the example 1, and correspondingly the length of the upper half portion of the piece is also formed larger. Thus, the overall length of the piece is formed relatively long as compared to the outer diameter thereof.

With this piece, the outer diameter of the tip end portion 4 connected to the upper end portion of the coupling shaft 8 can be made smaller, and thus an electrode catheter of 5 Fr (about 1.7 mm) or smaller can be easily realized. Further, since the chamfer 30 as an inclined surface is provided on the lower side of the end portion of each short shaft 21, what is made easy is the operation of coupling the pieces utilizing elastic deformation property of the support arm portions 28 of each piece to be coupled.

The catheter of the present invention can, for example, be used for cardiac pacing and/or mapping in patients with cardiac diseases such as arrhythmia or heart failure. When used for pacing and/or mapping, the catheter is used by the following method, though the method shall not be limited to the one shown below.

1. Incise the skin over the femoral vein.
2. Insert the catheter of the present invention into the lumen of the femoral vein from outside the incision to place the electrodes in the lumen of an affected or observation area of the heart by following the vein from the femoral vein.
3. Connect the catheter to, for example, a pulse generator or a pacing system analyzer via an extension cable or the like extended from a terminal part of the catheter.
4. Perform pacing and/or mapping at the affected or observation area of the heart.
5. Remove the catheter of the present invention after completing pacing and/or mapping at the affected or observation area of the heart.
6. Suture the incision over the femoral vein.

If used for cardiac pacing and/or mapping, rather than the femoral vein, there can also be employed a method of percutaneously puncturing or incising the left or right cephalic vein to make it to the subclavian vein or internal jugular vein. Usually, the left subclavian vein or the right internal jugular vein is used.

As explained in detail above, the electrode catheter of the present invention is such that the tip end portion thereof can be curved at any or a desired curvature radius, whereby the catheter of the invention can be inserted through curved vascular lumens. Further, the electrodes can be precisely brought into contact with the affected area of the heart. Therefore, a highly accurate and precise mapping and/or pacing of the affected area is possible for diagnosis and/or treatment of diseases such as arrhythmia and heart failure by electrophysiological testing.

Further, the electrode catheter of the present invention can also be used as an ablation catheter in the treatment of arrhythmias and other disorders, and also as an esophageal temperature sensor for preventing causing complications such as injuries due to esophageal overheating during cardiac ablation procedures.

Furthermore, the electrode catheter of the present invention can also be used as a catheter for defibrillation, where bending at a small curvature radius is required for indwelling the catheter in the coronary sinus.

Although the present invention has been described above with examples, the invention is not limited to the examples described above, and various modified examples can be implemented within the scope of the gist of the invention. For example, the number, outer diameters and lengths of the pieces as the composing elements of the coupling shaft can be changed as needed. Further, it is also possible to partially change the curvature radius of the tip end portion by coupling together multiple types of pieces with different dimensions from the center of the rotation shaft of the piece to the center of the shaft receiving hole thereof.

DESCRIPTION OF THE SYMBOLS

1 Electrode catheter
2 Catheter main body
3 Operation handle
4 Tip end portion
8 Coupling shaft
9 Electrode (ring electrode)
10 Outer tube
12 Piece
13 Head member
14 Operation wire
15 Operation wire
17 Lead wire
18 Gap
21 Rotation shaft (short shaft)
22 Shaft receiving hole
23 Through hole
25 Cutout

What is claimed is:

1. An electrode catheter comprising:

a catheter main body;

an operation handle connected to a base end side of the catheter main body; and a tip end portion connected to a tip end side of the catheter main body, wherein the tip end portion has:

an outer tube with a plurality of electrodes being provided and spaced apart on an outer circumferential surface thereof;

a coupling shaft with a plurality of pieces being coupled so that the pieces are able to mutually rotate within a predetermined range in a hollow space of the outer tube;

a head member connected to a tip end of the coupling shaft; and a plurality of operation wires with one ends thereof being fixed to the head member and the other ends thereof being fixed to the operation handle, wherein the plurality of pieces are made by a synthetic resin, and the plurality of pieces each have;

a rotation shaft that is provided on both surfaces of a central plate portion formed at a lower half portion of the respective piece in a longitudinal direction of the coupling shaft, and protrudes in a direction orthogonal to a short axis center of the coupling shaft;

a shaft receiving hole that is provided on a pair of support arm portions formed at an upper half portion of the piece in the longitudinal direction of the coupling shaft, and axially supports the rotation shaft; and a through hole that is located at a position offset from the axis center, and an inclined surface is formed on the inner surface of the pair of support arm portions of respective piece, and the circumferential side surface of the rotation shaft is rounded in shape, and wherein one of the operation wires is inserted through the through hole, and the tip end portion is allowed to be curved by operating the operation wires via the operation handle.

2. An electrode catheter comprising:

a catheter main body;

an operation handle connected to a base end side of the catheter main body; and a tip end portion connected to a tip end side of the catheter main body, wherein the tip end portion has:

an outer tube with a plurality of electrodes being provided and spaced apart on an outer circumferential surface thereof;

a coupling shaft with a plurality of pieces being coupled so that the pieces are able to mutually rotate within a predetermined range in a hollow space of the outer tube;

a head member connected to a tip end of the coupling shaft; and a plurality of operation wires with one ends thereof being fixed to the head member and the other ends thereof being fixed to the operation handle, wherein the plurality of pieces are made by a synthetic resin, and the plurality of pieces each have;

a rotation shaft that is provided on both surfaces of a central plate portion formed at a lower half portion of the respective piece in a longitudinal direction of the coupling shaft, and protrudes in a direction orthogonal to a short axis center of the coupling shaft;

a shaft receiving hole that is provided on a pair of support arm portions formed at an upper half portion of the piece in the longitudinal direction of the coupling shaft, and axially supports the rotation shaft; and a through hole that is located at a position offset from the axis center, and a chamfer as an inclined surface is provided on the lower side of the end of respective rotation shaft, and wherein one of the operation wires is inserted through the through hole, and the tip end portion is allowed to be curved by operating the operation wires via the operation handle.

* * * * *